(12) United States Patent
Valmori et al.

(10) Patent No.: US 6,384,190 B1
(45) Date of Patent: *May 7, 2002

(54) ISOLATED DECAPEPTIDES WHICH BIND TO HLA MOLECULES

(75) Inventors: Danila Valmori, Lausanne; Jean-Charles Cerottini; Pedro Romero, both of Epalinges, all of (CH)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/461,083

(22) Filed: Dec. 14, 1999

Related U.S. Application Data

(62) Division of application No. 08/880,963, filed on Jun. 23, 1997, now Pat. No. 6,025,470.

(51) Int. Cl.[7] ........................ A01N 37/34; A61K 31/275
(52) U.S. Cl. ........................................... 530/328
(58) Field of Search .................................... 530/328

(56) References Cited

U.S. PATENT DOCUMENTS

| | | |
|---|---|---|
| 5,487,974 A | 1/1996 | Boon-Falleur et al. |
| 5,554,506 A | 9/1996 | van der Bruggen et al. |
| 5,554,724 A | 9/1996 | Melief et al. |
| 6,025,470 A * | 2/2000 | Valmori et al. |

FOREIGN PATENT DOCUMENTS

| | | |
|---|---|---|
| WO | WO9529193 | 11/1995 |

OTHER PUBLICATIONS

DiBrino et al. J. Immunol. vol. 151(11):5930–5935, 1993.*
pir Accession No, S09648, 1993.*
ags Accession No. R90776, 1996.*
Biosis Accession No. 1996: 317109, 1996.*
Embase Accession No. 9515161, 1995.*
Romero et al., "Cytolytic T Lymphocyte Recognition of the Immunodominant HLA–A *0201–Restricted Melan–A/MART–1 Antigenic peptide in Melanoma", J. Immunol., 159:2366–2374 (1997).
Rammensee et al., "MHC Ligands and peptide Motifs: First Listing," Immunogenics, 41:178–228 (1995).
Loftus et al., "Identification of Epitope Mimics Recognized by CTL Reactive to the Melanoma/Melanocyte–derived Peptide MART–1 (27–35)," J. Exp. Med. 184:647–657 (1996).

Wölfel et al., "Two tyrosinase nonapeptides recognized on HLA–A2 melanomas by autologous cytolytic T lymphocytes," Eur. J. Immunol., 24:759–764 (1994).
Wölfel et al., "Analysis of Antigens Recognized on Human Melanoma Cells by A2 Restricted Cytolytic T Lymphocytes," Int. j. Cancer, 55:237–244 (1993).
Van der Bruggen et al., "A peptide encoded by human gene MAGE–3 and presented by HLA–A2 induces cytolytic T lymphocytes that recognize tumor cells expressing MAGE–3," Eur. J. Immunol., 24:3038–3043 (1994).
Slinguff et al., "Recognition of Human Melanoma Cells by HLA–A2.1 Restricted Cytolytic T Lymphocytes Is Mediated By At Least Six Shared Peptide Epitopes," J. Immunol. 150(7):2955–2963 (1993).
Ruppert et al., "Prominent role of Secondary anchor Residues In Peptide binding to HLA–A2.1 Molecules," Cell 74:929–937 (1993).
Hunt et al., "Characterization of peptides bound to the Class–1 MHC Molecules HLA–A2.1 By mass Spectometry," Science, 255:1261–1263 (1992).
Falk et al., "Allele Specific Motifs Revealed by Sequencing of Self Peptides Eluted From MHC Molecules," Nature, 351:290–296 (1991).
Valmori et al., "Enhanced Generation of Specific Tumor–Reactive CTL In Vitro by Selected Melan–A/MART–1 immunodominant peptide Analogues", j. Immunol., 160:1750–1758 (1998).
Anichini et al., "Cytolyltic T Cells Directed to tumor Antigens Not Expressed On Normal Melanocytes Dominate HLA–A2.1 Restricted Immune Repertoire To Melanoma," J. Immunol., 156–208–217 (1996).
Ochoa–Garay, et al., "The Ability of Peptides to Induce Cytotoxic T Cells In Vitro Does Not Strongly Correlate With Their Afinity for the H–2Ld Molecule: Implications For Vaccine Design And Immunotherapy." Mol Immunol. 34(3)273–281, 1997.

* cited by examiner

Primary Examiner—David Saunders
Assistant Examiner—Amy DeCloux
(74) Attorney, Agent, or Firm—Fulbright & Jaworski, LLP

(57) ABSTRACT

Nonapeptides and decapeptides which bind to HLA molecules and provoke proliferation of cytolytic T cells are disclosed. The decapeptides terminate in Valine, and are restricted in their first three amino acid positions. Other useful nonapeptides are also disclosed.

6 Claims, 4 Drawing Sheets

Induction of Melan-A specific, tumor reactive CTL by *in vitro* stimulation with Melan-A peptide analogs

SEQUENCE LISTING

```
<160> NUMBER OF SEQ ID NOS: 21

<210> SEQ ID NO 1
<211> LENGTH: 10
<212> TYPE: PRT
<213> ORGANISM: Artificial sequence
<220> FEATURE:
<223> OTHER INFORMATION: Peptide based on Melan -A peptide

<400> SEQUENCE: 1

Glu Ala Ala Gly Ile Gly Ile Leu Thr Val
 1               5                   10

<210> SEQ ID NO 2
<211> LENGTH: 9
<212> TYPE: PRT
<213> ORGANISM: Artificial Sequence
<220> FEATURE:
<223> OTHER INFORMATION: Peptide derived from M elan A

<400> SEQUENCE: 2

Ala Ala Gly Ile Gly Ile Leu Thr Val
 1               5

<210> SEQ ID NO 3
<211> LENGTH: 10
<212> TYPE: PRT
<213> ORGANISM: Artificial Sequence
<220> FEATURE:
<223> OTHER INFORMATION: Peptide based on Melan  A protein

<400> SEQUENCE: 3

Ala Ala Gly Ile Gly Ile Leu Thr Val Ile
 1               5                   10

<210> SEQ ID NO 4
<211> LENGTH: 9
<212> TYPE: PRT
<213> ORGANISM: Artificial Sequence
<220> FEATURE:
<223> OTHER INFORMATION: Peptide based on Melan  A protein

<400> SEQUENCE: 4

Ile Leu Thr Val Ile Leu Gly Val Leu
 1               5

<210> SEQ ID NO 5
<211> LENGTH: 9
<212> TYPE: PRT
<213> ORGANISM: Artificial Sequence
<220> FEATURE:
<223> OTHER INFORMATION: Derivative of SEQ ID NO: 2
```

```
<400> SEQUENCE: 5

Ala Leu Gly Ile Gly Ile Leu Thr Val
 1               5

<210> SEQ ID NO 6
<211> LENGTH: 9
<212> TYPE: PRT
<213> ORGANISM: Artificial Sequence
<220> FEATURE:
<223> OTHER INFORMATION: Derivative of SEQ ID NO: 2

<400> SEQUENCE: 6

Ala Met Gly Ile Gly Ile Leu Thr Val
 1               5

<210> SEQ ID NO 7
<211> LENGTH: 9
<212> TYPE: PRT
<213> ORGANISM: Artificial Sequence
<220> FEATURE:
<223> OTHER INFORMATION: Derivative of SEQ ID NO: 2

<400> SEQUENCE: 7

Leu Ala Gly Ile Gly Ile Leu Thr Val
 1               5

<210> SEQ ID NO 8
<211> LENGTH: 9
<212> TYPE: PRT
<213> ORGANISM: Artificial Sequence
<220> FEATURE:
<223> OTHER INFORMATION: Derivative of SEQ ID NO: 2

<400> SEQUENCE: 8

Met Ala Gly Ile Gly Ile Leu Thr Val
 1               5

<210> SEQ ID NO 9
<211> LENGTH: 10
<212> TYPE: PRT
<213> ORGANISM: Artificial Sequence
<220> FEATURE:
<223> OTHER INFORMATION: Derivative of SEQ ID NO: 1

<400> SEQUENCE: 9

Glu Leu Ala Gly Ile Gly Ile Leu Thr Val
 1               5                  10

<210> SEQ ID NO 10
<211> LENGTH: 10
<212> TYPE: PRT
<213> ORGANISM: Artificial sequence
<220> FEATURE:
<223> OTHER INFORMATION: Derivative of SEQ ID NO: 1

<400> SEQUENCE: 10

Glu Met Ala Gly Ile Gly Ile Leu Thr Val
 1               5                  10

<210> SEQ ID NO 11
<211> LENGTH: 10
<212> TYPE: PRT
<213> ORGANISM: Artificial sequence
<220> FEATURE:
<223> OTHER INFORMATION: Derivative of SEQ ID NO: 1
```

-continued

```
<400> SEQUENCE: 11

Glu Ala Leu Gly Ile Gly Ile Leu Thr Val
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Derivative of SEQ ID NO: 1

<400> SEQUENCE: 12

Glu Ala Met Gly Ile Gly Ile Leu Thr Val
 1               5                  10

<210> SEQ ID NO 13
<211> LENGTH: 10
<212> TYPE: PRT
<213> ORGANISM: Artificial sequence
<220> FEATURE:
<223> OTHER INFORMATION: Derivative of SEQ ID NO: 1

<400> SEQUENCE: 13

Tyr Ala Ala Gly Ile Gly Ile Leu Thr Val
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Derivative of SEQ ID NO: 1

<400> SEQUENCE: 14

Phe Ala Ala Gly Ile Gly Ile Leu Thr Val
 1               5                  10

<210> SEQ ID NO 15
<211> LENGTH: 10
<212> TYPE: PRT
<213> ORGANISM: Artificial sequence
<220> FEATURE:
<223> OTHER INFORMATION: Derivative of SEQ ID NO: 1

<400> SEQUENCE: 15

Ala Ala Ala Gly Ile Gly Ile Leu Thr Val
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Derivative of SEQ ID NO: 1

<400> SEQUENCE: 16

Ala Leu Ala Gly Ile Gly Ile Leu Thr Val
 1               5                  10

<210> SEQ ID NO 17
<211> LENGTH: 9
<212> TYPE: PRT
<213> ORGANISM: H. influenzae
<220> FEATURE:
<223> OTHER INFORMATION: Portion of Influenza A mat

```
Glu Ile Leu Gly Phe Val Phe Thr Leu
  1               5

<210> SEQ ID NO 18
<211> LENGTH: 9
<212> TYPE: PRT
<213> ORGANISM: Artificial Sequence
<220> FEATURE:
<223> OTHER INFORMATION: Portion of Influenza A  matrix protein

<400> SEQUENCE: 18

Gly Val Asp Pro Ile Gly His Leu Tyr
  1               5

<210> SEQ ID NO 19
<211> LENGTH: 9
<212> TYPE: PRT
<213> ORGANISM: Artificial Sequence
<220> FEATURE:
<223> OTHER INFORMATION: Peptide from protein M AGE-3

<400> SEQUENCE: 19

Phe Leu Trp Gly Pro Arg Ala Leu Val
  1               5

<210> SEQ ID NO 20
<211> LENGTH: 10
<212> TYPE: PRT
<213> ORGANISM: Artificial Sequence
<220> FEATURE:
<221> NAME/KEY: MUTAGEN
<222> LOCATION: 2...9
<223> OTHER INFORMATION: Dervative of SEQ ID NO:1.  Amino acid 1 is
      Ala, Tyr or Phe; Amino Acid 2  is Ala or Leu
      amino acids 3-9 can be any am ino acid

<400> SEQUENCE: 20

Xaa Xaa Xaa Xaa Xaa Xaa Xaa Xaa Xaa Val
  1               5                  10

<210> SEQ ID NO 21
<211> LENGTH: 10
<212> TYPE: PRT
<213> ORGANISM: Artificial Sequence
<220> FEATURE:
<221> NAME/KEY: MUTAGEN
<222> LOCATION: 2...9
<223> OTHER INFORMATION: Derivative of SEQ ID NO:1.  Amino acids 4-9
      are any amino acid. Amino acids 2 and 3 can be Ala Leu or Met,
      but if amino acid 2 is Ala, amino acid 3 must be Leu or Met.
      If amino acid 3 is Ala, amino  acid 2 must be
      Leu or Met.

<400> SEQUENCE: 21

Glu Xaa Xaa Xaa Xaa Xaa Xaa Xaa Xaa Val
  1               5                  10
```

ISOLATED DECAPEPTIDES WHICH BIND TO HLA MOLECULES

This application is a divisional Ser. No. 08/880,963, filed Jun. 23, 1997, now U.S. Pat. No. 6,025,470, incorporated by reference.

FIELD OF THE INVENTION

This invention relates to peptides which are useful in the context of cellular immunology. More particularly, the invention relates to peptides which bind to HLA molecules on the surface of cells. At least some of these peptides also induce the activation of cytolytic T cells, when they are complexed with their partner HLA molecule. Also a part of the invention are the uses of these peptides in areas such as identifying HLA-A2 positive cells, provoking T cells, determining presence of particular T cells, as well as cytolytic T cells themselves.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum⁻ variants fail to form progressive tumors because they initiate an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the tumor rejection antigens are lysed. Characterization studies have identified CTL clones which specifically lyse cells expressing the tumor rejection antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immnunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum–" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum+, such as the line referred to as "P1", and can be provoked to produce tum⁻ variants. Since the tum⁻ phenotype differs from that of the parent cell line, one expects a difference in the DNA of tum⁻ cell lines as compared to their tum+ parental lines, and this difference can be exploited to locate the gene of interest in tum⁻ cells. As a result, it was found that genes of tum variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by H-$2^d$ Class I molecules for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254:1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991) and De Plaen, et al., Immunogenetics 40: 360 (1994). The mechanism by which a protein is processed and presented on a cell surface has now been fairly well documented. A cursory review of the development of the field may be found in Barinaga, "Getting Some 'Backbone': How MHC Binds Peptides", Science 257: 880 (1992); also, see Fremont et al., Science 257: 919 (1992); Matsumura et al., Science 257: 927 (1992); Engelhard, Ann. Rev. Immunol 12:181–207 (1994); Madden, et al, Cell 75:693–708 (1993); Ramensee, et al, Ann. Rev. Immunol 11:213–244 (1993); German, Cell 76: 287–299 (1994). These papers generally point to a requirement that the peptide which binds to an MHC/HLA molecule be nine amino acids long (a "nonapeptide"), and to the importance of the second and ninth residues of the nonapeptide. For H-$2K^b$, the anchor residues are positions 5 and 8 of an octamer, for H-$2D^b$, they are positions 5 and 9 of a nonapeptide while the anchor residues for HLA-A1 are positions 3 and 9. of a nonamer. Generally, for HLA molecules, positions 2 and 9 are anchors.

Studies on the MAGE family of genes have now revealed that a particular nonapeptide is in fact presented on the surface of some tumor cells, and that the presentation of the nonapeptide requires that the presenting molecule be HLA-A1. Complexes of the MAGE-1 tumor rejection antigen (the "TRA" or nonapeptide") leads to lysis of the cell presenting it by cytolytic T cells ("CTLs").

Research presented in, e.g., U.S. Pat. No. 5,405,940 filed Aug. 31, 1992, and in U.S. Pat. No. 5,571,711, found that when comparing homologous regions of various MAGE genes to the region of the MAGE-1 gene coding for the relevant nonapeptide, there is a great deal of homology. Indeed, these observations lead to one of the aspects of the invention disclosed and claimed therein, which is a family of nonapeptides all of which have the same N-terminal and C-terminal amino acids. These nonapeptides were described as being useful for various purposes which includes their use as immunogens, either alone or coupled to carrier peptides. Nonapeptides are of sufficient size to constitute an antigenic epitope, and the antibodies generated thereto were described as being useful for identifying the nonapeptide, either as it exists alone, or as part of a larger polypeptide.

The preceding survey of the relevant literature shows that various peptides, usually eight, nine, or ten amino acids in length, complex with MHC molecules and present targets for recognition by cytolytic T cells. A great deal of study has been carried out on melanoma, and melanoma antigens which are recognized by cytolytic T cells are now divided into three broad categories. The first, which includes many of the antigens discussed, supra, (e.g., MAGE), are expressed in some melanomas, as well as other tumor types, and normal testis and placenta. The antigens are the expression product of normal genes which are usually silent in normal tissues.

A second family of melanoma antigens includes antigens which are derived from mutant forms of normal proteins. Examples of this family are MUM-1 (Coulie, et al, Proc. Natl. Acad. Sci. USA 92:7976–7980 (1995)); CDK4 (Wölfel, et al, Science 269:1281–1284(1955)); Bcatenin (Robbins, et al, J. Exp. Med. 183:1185–1192 (1996)); and HLA-2 (Brandel, et al, J. Exp. Med. 183:2501–2508 (1996)). A third category, also discussed, supra, includes the differentiation antigens which are expressed by both melanoma and melanocytes. Exemplary are tyrosinase gp100, gp75, and Melan A/Mart-1. See U.S. Pat. No. 5,620,886 incorporated by reference, with respect to Melan-A. See Wölfel, et al., Eur. J. Immunol. 24: 759 (1994) and Brichard, et al., Eur. J. Immunol. 26: 224 (1996) for tyrosinase; Kang, et al., J. Immunol. 155: 1343 (1995); Cox, et al., Science 264: 716 (1994); Kawakami, et al., J. Immunol. 154: 3961 (1995) for gp 100; Wang, et al., J. Exp. Med. 183: 1131 (1996) for gp 75.

Cytolytic T cells ("CTLs" hereafter) have been identified in peripheral blood lymphocytes, and tumor infiltrating lymphocytes, of melanoma patients who are HLA-A*0201 positive. See Kawakami, et al, Proc. Natl. Acad. Sci. USA 91:3515 (1994); Coulie, et al, J. Exp. Med. 180:35 (1994). When ten HLA-A*0201 restricted Melan-A specific CTLs were derived from different patients were tested, nine of them were found to recognize and react and the peptide Ala Ala Gly Ile Gly lie Leu Thr Val, (SEQ ID NO:2), which consists of amino acids 27–35 of Melan-A. (Kawakami, et al, J. Exp. Med 180:347–352 (1994)). Rivoltini, et al, J. Immunol 154:2257 (1995), showed that Melan-A specific CTLs could be induced by stimulating PBLs from HLA-A*0201 positive normal donors, and melanoma patients, using SEQ ID NO:2. The strength of this response has led to SEQ ID NO:2 being proposed as a target for vaccine development. It has now been found, however, that a decapeptide, i.e., Glu Ala Ala Gly Ile Gly Ile Leu Thr Val (SEQ ID NO:1), is actually a better target than SEQ ID NO:2. This recognition has led to work set forth herein, which is part of the invention.

The majority of peptides which have been identified as binding to HLA-A*0201 are 9 or 10 amino acids in length, and are characterized by two anchor residues. The first is Leu or Met at position 2, and the second is Leu or Val at position 9. See Falk, et al, Nature 351:290 (1991). Ruppert, et al, in Cell 74:929 (1993), show that amino acids found at other positions within a nona- or decapeptide may also have a role in the peptide -HLA-A*0201 interaction. They show, e.g., that a negatively charged residue or proline at position 1 was associated with poor HLA-A*0201 binding.

What is interesting about this work is that the two peptides represented by SEQ ID NOS:1 and 2 do not possess the major anchor residue at position 2 and, the strong binder SEQ ID NO:1 has a negative residue at position 1.

A strong binder is not necessarily a stable binder, meaning that the interaction between peptide and HLA molecule may be, and is, brief. When it is desired to induce CTLs, to identify them or to carry out other types of experiments, it would be desirable to have a peptide with the ability to bind to an MHC Class I molecule which binds with high affinity and forms stable complexes.

The invention involves, inter alia, the development of new nonamers and decamers which are surprisingly good HLA binders and CTL stimulators. These molecules, as well as their uses, are among the features of the invention which are set forth in the disclosure which follows.

DETAILED DESCRIPTION OF PREFERRED EMBODIMENTS

EXAMPLE 1

In these experiments tumor infiltrating lymphocytes ("TILs" hereafter), were generated from tumor invaded lymph nodes of patients who were HLA-A*0201 positive. The experiments were designed so as to avoid antigen specific selection in vitro, and the methodology is now set forth.

Figure 1:
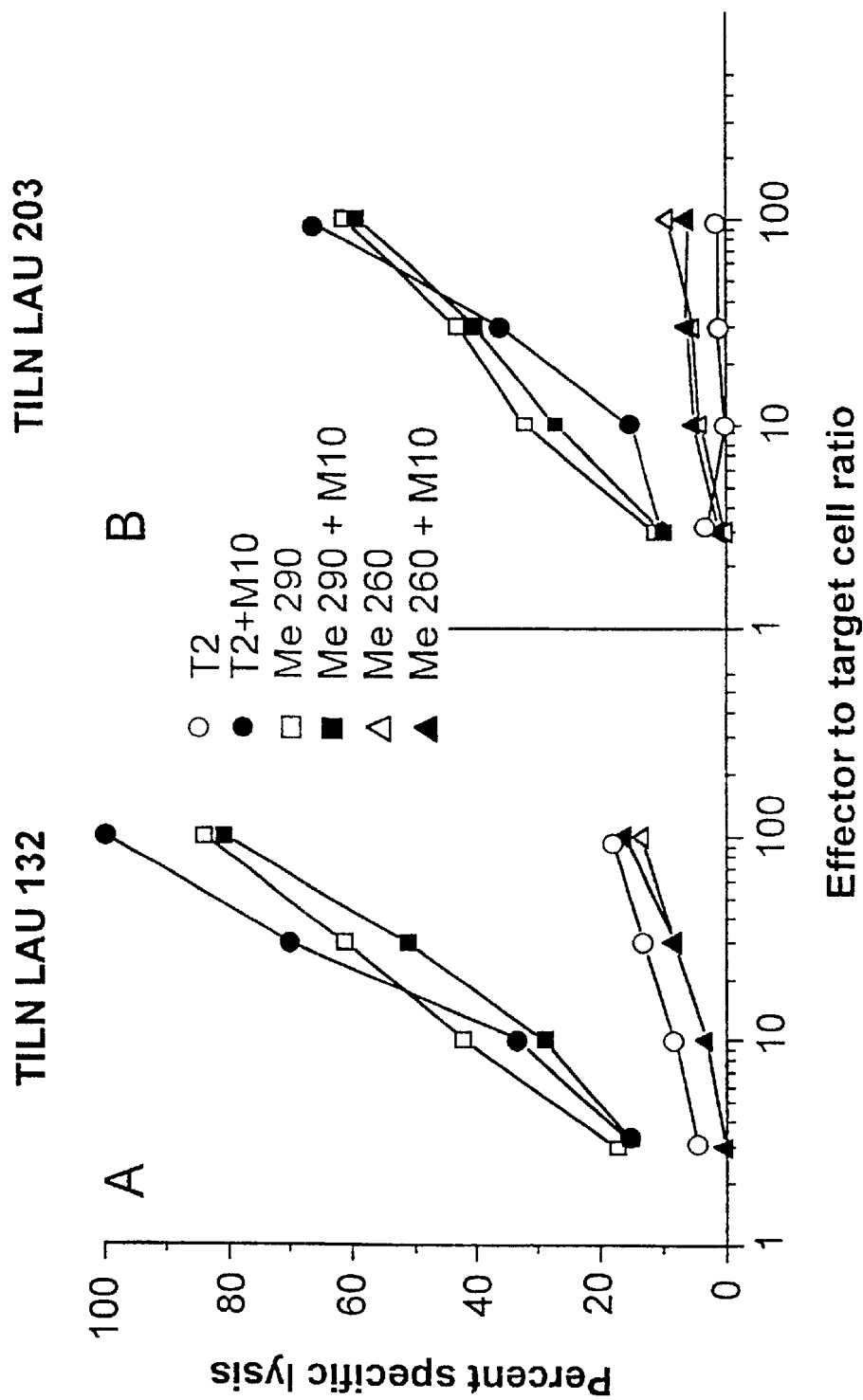
FIGS. 1A and 1B i.e. show results of experiments carried out to determine if tumor infiltrating lymphocyte populations would lyse cells presenting complexes of HLA-A*0201 and various peptides on their surfaces.

Biopsies of tumor infiltrated lymph nodes ("TILNs" hereafter) were lysed to single cell suspensions, and then cultured in 24 well culture plates. A total of 50 µl of cell suspension was added to 2 mls of Iscove's Dulbecco medium which had been supplemented with Asn (0.24 mM), Arg (0.55 mM), and Gln (1.5 mM), and 10% pooled human A$^+$ serum (serum obtained from type A blood donors), together with recombinant human IL-2 (100 u/ml), and IL-7 (10 ng/ml). These were the only cytokines used to culture the cell suspensions, so as to avoid antigen specific selection in vitro. The suspensions were cultured for 2–3 weeks, and the cells were then characterized for cell surface phenotype. Only populations with greater than 75% CD8$^+$T cells, and of desired cytolytic activity were used. This second property was determined by combining the TILN populations with autologous cells, a melanoma cell line previously characterized as being HLA-A*0201 positive (Me290), a melanoma cell line known to be HLA-A*0201 negative (Me260) or cell line T2, which does not process antigen, together with the peptide of SEQ ID NO:1. The peptide was added at 1 µM, together with varying ratios of effector (TILN) cells, and the target cells. The results presented in FIG. 1, show results obtained using LAU 132 and LAU 203, two TILN populations identified via this method. In FIG. 1, "M10" is SEQ ID NO:1, and the additional abbreviations are as set forth, supra. The assay was a 4 hour $^{51}$Cr release assay, carried out in the absence or presence of exogenously added peptide. In FIG. 1, open symbols stand for the absence of the peptide, and solid symbols for its presence. In this assay, the target cells were labelled with $^{51}$Cr for one hour, at 37° C., and were then washed two times. Labelled cells (1000 cells in 50 µl) were added to a 50 µl sample of effector cells (varying amounts, as indicated herein), in the presence or absence of 50 µl of antigenic peptide (1 µg/ml). Prior to their addition, the effector cells had been incubated for a minimum of 20 minutes at 37° C., in the presence of unlabelled natural killer (NK) cells (50,000 cells per well), in order to eliminate any non-specific lysis due to NK-like effectors present in the effector population. The $^{51}$Cr release was measured after 4 hours of incubation at 37° C., and percent specific lysis was calculated as:

$$100\left[\frac{(\text{experimental release} - \text{spontaneous release})}{\text{total} - \text{spontaneous release}}\right]$$

As FIG. 1 shows, the two TILN populations lysed the HLA-A*0201 positive cell line equally well, whether or not the peptide was added. The HLA-A*0201 negative line, Me260, was not lysed in either situation, and T2, which does not process antigen, was lysed only when the peptide was added. These results show that the two TILN populations used hereafter recognize the epitope defined by SEQ ID NO:1, when complexed to HLA-A*0201 positive cells.

EXAMPLE 2

The experiments described, supra, were modified somewhat, to determine if the TILNs recognized other peptides better than SEQ ID NO:1. In these experiments, the following peptides were synthesized, using known methods:

Ala Ala Gly Ile Gly Ile Leu Thr Val (SEQ ID NO:2)
Ala Ala Gly Ile Gly Ile Leu Thr Val Ile (SEQ ID NO:3)
Ile Leu Thr Val Ile Leu Gly Val Leu (SEQ ID NO:4)

These peptides correspond, respectively, to amino acids 27–35, 27–36, and 32–40 of Melan-A.

TIL recognition was determined by incubating T2 cells (target), with TILs (effector), at an effector: target ratio of 30:1. Varying concentrations of the peptides SEQ ID NOS:1, 2, 3 or 4 were used. The $^{51}$Cr release assay discussed, supra, was used. The following Table sets forth the results of these experiments, wherein the peptide concentration is that which gave 50% of maximum activity. Relative activity is that obtained via comparison to SEQ ID NO:2, i.e.: [nM]50% [SEQ ID NO:2][nM]50%][test peptide].

TABLE I

|  | TILN LAU 203 | | TILN LAU 132 | |
|---|---|---|---|---|
| Peptide Sequence | Peptide$^a$ [nM] 50% | Relative activity$^b$ | Peptide [nM] 50% | Relative activity |
| AAGIGILTV$_{27-35}$ SEQ ID NO:2 | 40 | 1 | 15 | 1 |
| EAAGIGILTV$_{26-35}$ SEQ ID NO:1 | 1.5 | 27 | 1 | 15 |
| AAGIGILTVI$_{27-36}$ SEQ ID NO:3 | 600 | 0.06 | 300 | 0.05 |
| ILTVILGV$_{32-40}$ SEQ ID NO:4 | >10$^4$ | <4 × 10$^{-3}$ | >10$^4$ | <1.5 × 10$^{-3}$ |

It will be seen that SEQ ID NO:1 had significantly higher activity than the other peptides tested.

EXAMPLE 3

A series of peptides were then synthesized, in order to attempt to determine peptides with enhanced binding to HLA-A*0201 molecules. The peptides synthesized are considered to be derivatives of SEQ ID NO:2 (i.e., Ala Ala Gly Ile Gly Ile Leu Thr Val), and are Ala Leu Gly Ile Gly Ile Leu Thr Val (SEQ ID NO:5)
Ala Met Gly Ile Gly Ile Leu Thr Val (SEQ ID NO:6)
Leu Ala Gly Ile Gly Ile Leu Thr Val (SEQ ID NO:7)
and
Met Ala Gly Ile Gly Ile Leu Thr Val (SEQ ID NO:8)

For SEQ ID NO:1, i.e., Glu Ala Ala Gly Ile Gly Ile Leu Thr Val the derivatives were:

Glu Leu Ala Gly Ile Gly Ile Leu Thr Val (SEQ ID NO:9)
Glu Met Ala Gly Ile Gly Ile Leu Thr Val (SEQ ID NO:10)
Glu Ala Leu Gly Ile Gly Ile Leu Thr Val (SEQ ID NO:11)
Glu Ala Met Gly Ile Gly Ile Leu Thr Val (SEQ ID NO:12)
Tyr Ala Ala Gly Ile Gly Ile Leu Thr Val (SEQ ID NO:13)
Phe Ala Ala Gly Ile Gly Ile Leu Thr Val (SEQ ID NO:14)
Ala Ala Ala Gly Ile Gly Ile Leu Thr Val (SEQ ID NO:15) and
Ala Leu Ala Gly Ile Gly Ile Leu Thr Val (SEQ ID NO:16)

Three other control peptides were used, i.e.:

Glu Ile Leu Gly Phe Val Phe Thr Leu (SEQ ID NO:17)
Gly Val Asp Pro Ile Gly His Leu Tyr (SEQ ID NO:18) and
Phe Leu Trp Gly Pro Arg Ala Leu Val (SEQ ID NO: 19).

SEQ ID NOS: 17 and 18 correspond to amino acids 58–66 of Influenza A matrix protein ("FLUMA"), and amino acids 168–176 of MAGE-3 TRAP.

In these experiments a peptide known to bind to HLA-A*0201 was used, i.e. amino acids 271–279 of the MAGE-3 TRAP (SEQ ID NO:20), in an inhibition assay, together with cytolytic T cell line 198NS (Valmori, et al., Canc. Res. 57:735 (1997) which recognizes complexes of SEQ ID NO:20 and HLA-A*0201. In these assays, varying concentrations of test peptides (1 $\mu$M to 100 $\mu$M) were incubated with $^{51}$Cr labelled T2 cells (1000 cells/well), for 15 minutes, at room temperature. A suboptimal dose of SEQ ID NO:19 was then added (1 nM), together with CTL 198NS, in an amount sufficient to create a 5/1 effector/target ratio. A $^{51}$Cr release assay was then carried out, in accordance with the method set forth, supra. The amount of test peptide needed to inhibit recognition of complexes by the CTL was calculated, and then binding affinity of each peptide, relative to SEQ ID NO:2, was calculated, using the formula:

$$R = \frac{ID_{50}(\text{SEQ ID NO:2})}{ID_{50}(\text{test peptide})}$$

If R is greater than one, then the tested peptide bound to HLA-A*0201 with greater affinity than SEQ ID NO:2. A value less than one indicates lower affinity. The results are set forth below:

TABLE II

| Peptide | Sequence | Competitor[a] [$\mu$M] 50% | Relative competitor activity[b] |
|---|---|---|---|
| Melan-A$_{27-35}$ | AAGIGILTV SEQ ID NO:2 | 60 | 1 |
| | ALGIGILTV SEQ ID NO:5 | 1.5 | 40 |
| | AMGIGILTV SEQ ID NO:6 | 2 | 30 |
| | LAGIGILTV SEQ ID NO:7 | 65 | 1 |
| | MAGIGILTV SEQ ID NO:8 | 55 | 1 |
| MeLan-A$_{26-35}$ | EAAGIGILTV SEQ ID NO:1 | 5 | 4 |
| | ELAGIGILTV SEQ ID NO:9 | 6.5 | 9 |
| | EMAGIGILTV SEQ ID NO:10 | 20 | 3 |
| | EALGIGILTV SEQ ID NO:11 | 100 | 0.6 |
| | EAMGIGILTV SEQ ID NO:12 | 100 | 0.6 |
| | YAAGIGILTV SEQ ID NO:13 | 4 | 15 |
| | FAAGIGILTV SEQ ID NO:14 | 2 | 30 |
| Influenza A matrix$_{58-66}$ | GILGFVFTL SEQ ID NO:17 | 1 | 60 |
| MAGE-3$_{168-176}$ | EVDPIGHLY SEQ ID NO:20 | >100 | <0.6 |

SEQ ID NOS: 1, 5, 6, 9, 10, 13 and 14 all showed higher affinity than SEQ ID NO:2.

EXAMPLE 4

One concern in developing MHC binding peptides is that the resulting complexes of MHC molecule and peptide be stable, preferably more stable than the peptide originally found complexed to the MHC molecule.

To test stability of the newly synthesized peptides, T2 cells were incubated, overnight, at room temperature in serum free medium with saturating amounts of peptide (10 uM), and 3 $\mu$g/ml $\beta$-microglobulin, to facilitate the assembly of the requisite MHC molecules. Peptides were then removed, and $10^{-4}$M ementine (which inhibits protein synthesis) was added. The cells were then incubated at 37° C. for varying periods of time. Aliquots of cells were stained, at various points of the incubation, with a labelled HLA-A2 specific mAb to measure HLA-A2 expression.

Figure 2:
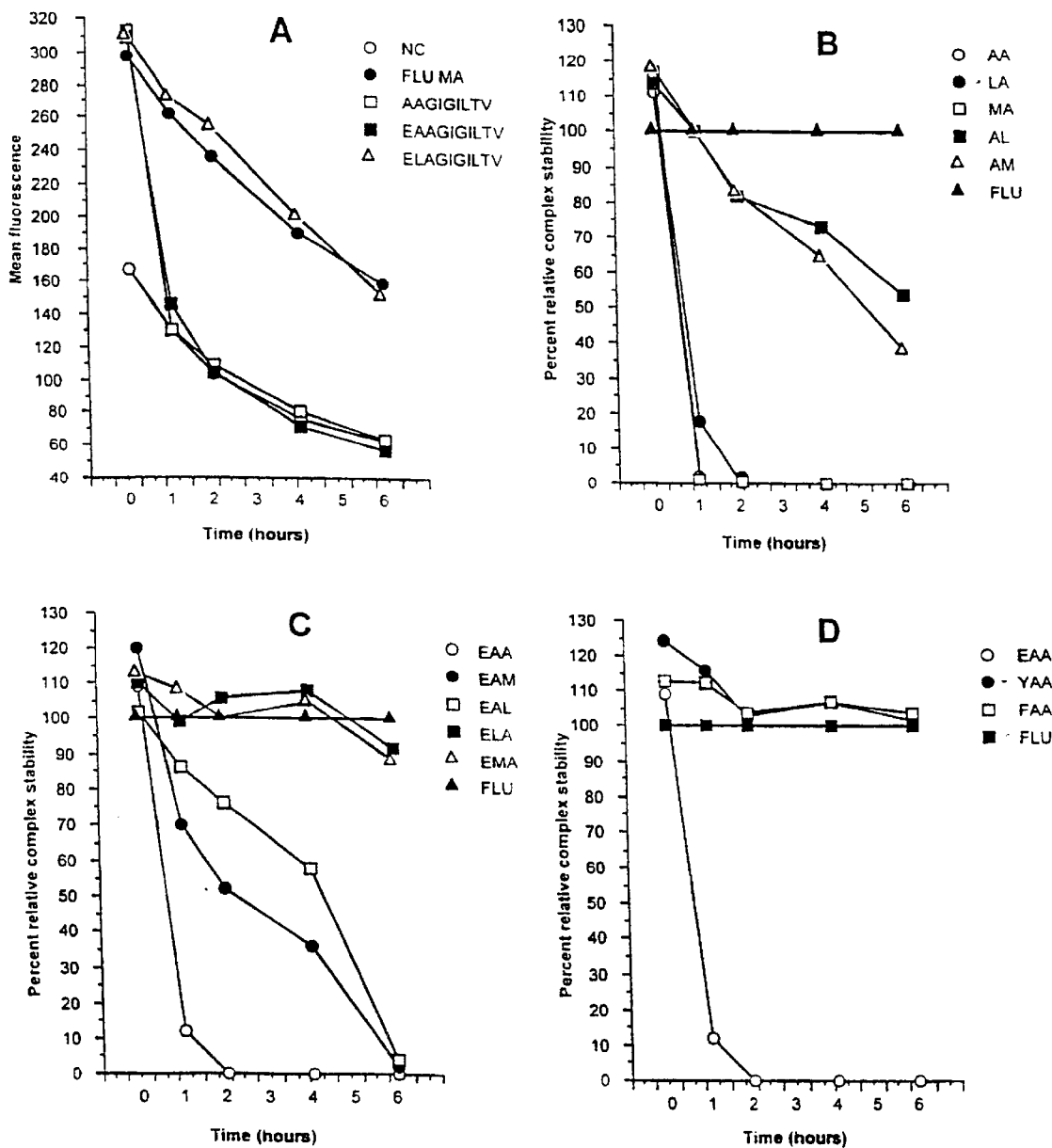
FIGS. 2A–2D show stability studies comparing various peptides.

Stability was determined by comparison with complexes involving SEQ ID NO:17 which were stable over a 6 hour period. The results are presented in FIGS. 2A–D. FIG. 2A shows show mean fluorescence intensity for each peptide. "NC" refers to HLA-A*0201, presented by T2 cells, in the absence of exogenous peptide, while "FLUMA" is SEQ ID NO:17, and is an acronym for "Flu matrix antigen." In FIG. 2A, the peptides are SEQ ID NOS: 2, 1 and 9. In FIG. 2B, they are SEQ ID NOS:2, 7, 8, 5, 6 and 17 ("FLUMA"). In FIG. 2C, they are SEQ ID NOS: 1, 12, 11, 9, 10 and 17. In FIG. 2D, they are SEQ ID NOS:1 13, 14 and 17. The breakup is solely to facilitate the review. FIGS. 2B–2D show relative complex stability where fluorescent intensities with test peptides were normalized, relative to the stability observed when using SEQ ID NO:17. SEQ ID NOS:1 and 2 both form unstable complexes, which decay within one hour. This was also found with SEQ ID NOS:7 and 8. On the other hand, SEQ ID NOS: 9, 10, 13 and 14 formed stable complexes over a 6 hour period, while SEQ ID NOS:5, 6, 11 and 12 formed complexes of intermediate stability.

EXAMPLE 5

The antigenic activity of each of the peptides presented, supra, when the peptide was associated with HLA-A*0201, was tested in a $^{51}$Cr assay of the type discussed, supra, using TILs, and CTLs. Dose response analyses were performed on each peptide, and antigenic activity, relative to SEQ ID NO:2, was calculated. These values are set forth in the following Tables III and IV and FIGS. 3 and 4 which present data from TILs, (Table III and FIG. 3) and CTLs (Table IV and FIG. 4), respectively.

Figure 3:
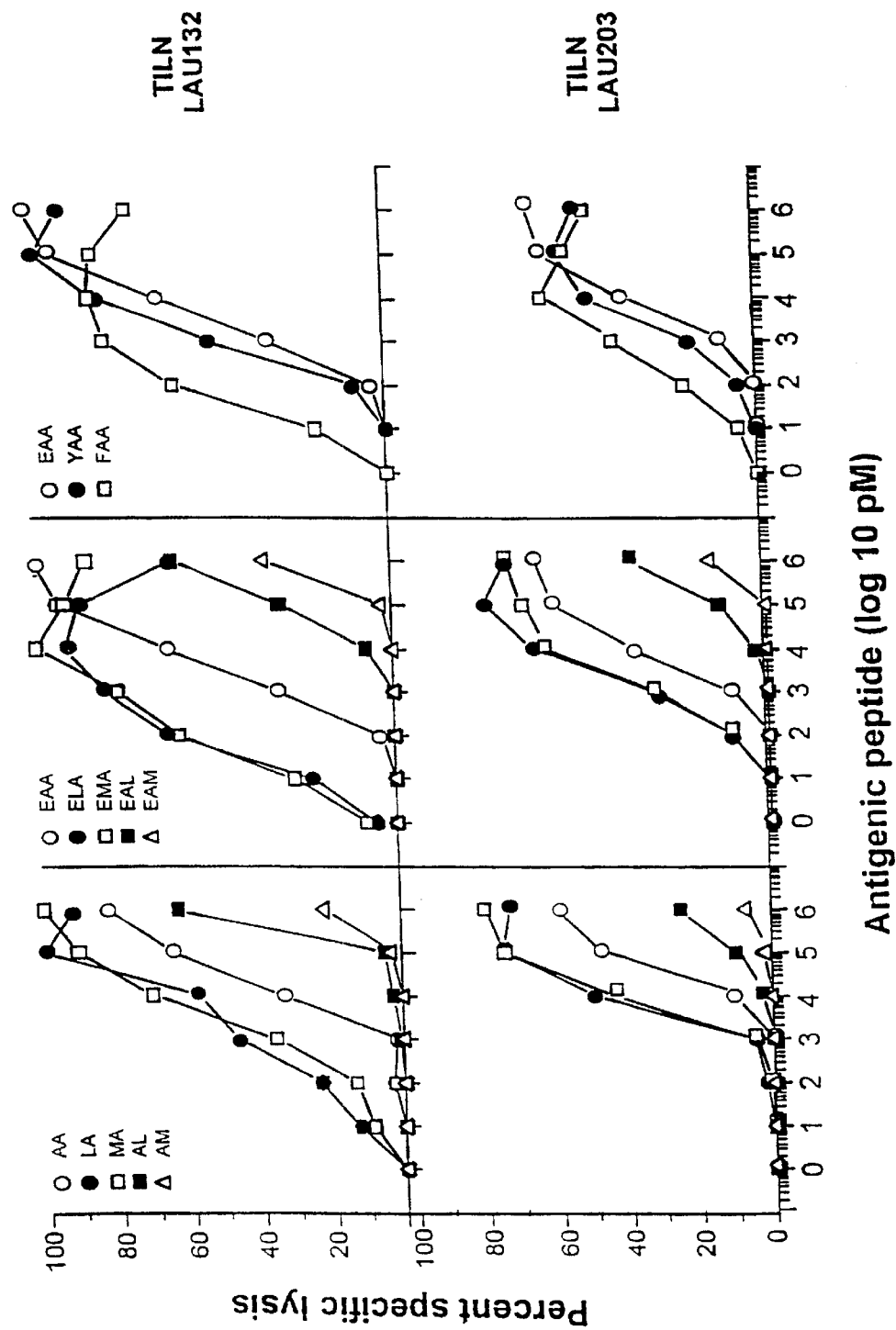
FIG. 3 shows antigenic activity of various peptides when tested with TILs.

Substituting Ala with Leu or Met enhanced activity between 7.5 and 20 fold, while substitutions at the second position nearly abolished it, even though binding to HLA-A*-0201 was increased (Table III and FIG. 3).

SEQ ID NO:1 was better recognized than SEQ ID NO:2, and substitution of Ala in the second position of SEQ ID NO:1 increased recognition 30- and 600 fold, respectively. Such substitutions at position 3 reduced activity, which was expected. Substitution of position 1 resulted in an increase in recognition.

TABLE III

| | TILN LAU 203 | | TILN LAU 132 | |
|---|---|---|---|---|
| Peptide Sequence | [nM] | Relative activity | [nM] | Relative activity |
| AAGIGILTV SEQ ID NO: 2 | 60 | 1 | 30 | 1 |
| ALGIGILTV SEQ ID NO: 5 | >1000 | <0.6 | >1000 | <0.03 |

TABLE III-continued

|  | TILN LAU 203 | | TILN LAU 132 | |
|---|---|---|---|---|
| Peptide Sequence | [nM] | Relative activity | [nM] | Relative activity |
| AMGIGILTV SEQ ID NO: 6 | >1000 | <0.6 | >1000 | <0.03 |
| LAGIGILTV SEQ ID NO: 7 | 6 | 10 | 1.5 | 20 |
| MAGIGILTV SEQ ID NO: 8 | 8 | 7.5 | 2.5 | 12 |
| EAAGIGILTV SEQ ID NO: 1 | 12 | 5 | 3 | 10 |
| ELAGIGILTV SEQ ID NO: 9 | 2 | 30 | 0.05 | 600 |
| EMAGIGILTV SEQ ID NO: 10 | 2 | 30 | 0.05 | 600 |
| EALGIGILTV SEQ ID NO: 11 | >1000 | <0.06 | >1000 | <0.03 |
| EAMGIGILTV SEQ ID NO: 12 | >1000 | <0.06 | >1000 | <0.03 |
| YAAGIGILTV SEQ ID NO: 13 | 5 | 20 | 1 | 30 |
| FAAGIGILTV SEQ ID NO: 14 | 1 | 60 | 0.05 | 600 |

The results obtained with CTLs are presented herein. Specifically, five independent HLA-A*0201 restricted Melan-A specific CTL clones were used, each of which is known to lyse melanoma target cells.

The CTLs recognized SEQ ID NO:2 with varying efficiency. When Leu was used to substitute Ala at position 1, four of the five clones showed enhanced recognition, while similar substitutions at position 2 resulted in a loss of activity. Three of the five clones recognized SEQ ID NO:1 more efficiently than SEQ ID NO:2, but all recognized SEQ ID NO:9 very efficiently, while recognition of SEQ ID NO:10 resulted in decreased efficiency of recognition to differing degrees, and SEQ ID NO:11 resulted in reduced recognition for four of five. When SEQ ID NO:12 was tested, it was surprising that recognition improved, because TIL recognition decreased. With respect to SEQ ID NOS: 13 and 14, there was reduced recognition by the CTLs.

It can be gathered from this that SEQ ID NOS: 7 and 9 were better recognized, consistently, than the other peptides tested, while other peptides were recognized different degrees.

EXAMPLE 6

Based upon the preceding data, the peptide of SEQ ID NO:9 was used for CTL induction studies.

In accordance with Valmori, et al, supra, peripheral blood lymphocytes from HLA-A*0201 positive melanoma patients were purified by centrifugation, and were enriched for CD3+ cells. The enriched subpopulation was then selected for CD8+ cells. The resulting subpopulations routinely contained better than 90% CD8+ cells, and these were used in further experiments.

The purified, CD8+ T cells were plated, at 1–2×10^6 cells/well, together with 2×10^6 stimulator cells, the preparation of which is discussed, infra. The effector and stimulator cells were combined in a total of 2 ml of Iscove's medium which had been supplemented with 10% human serum, L-arginine (0.55 mM), L-asparagine (0.24 mM), and L-glutamine (1.5 mM), together with recombinant human IL-7 (10 ng/ml).

To prepare the stimulator cells, 2×10^6 autologous PBLs were incubated for 2 hours, at 37° C., in serum free medium, with 20 µg/ml of each peptide and 3 µg/ml β-microglobulin. The PBLs were then washed, irradiated, (3000 rads), and then adjusted to an appropriate volume, before being added to the CD8+ cell populations. On day 7, cells were restimulated with peptide pulsed, autologous PBLs in complete medium, supplemented with 10 ng/ml of recombinant human IL-7, and 10 U/ml of recombinant human IL-2. There were weekly restimulations, using PBLs which were peptide pulsed and irradiated. CTL activity was tested for the first time after the second cycle (MC-2).

Figure 4:
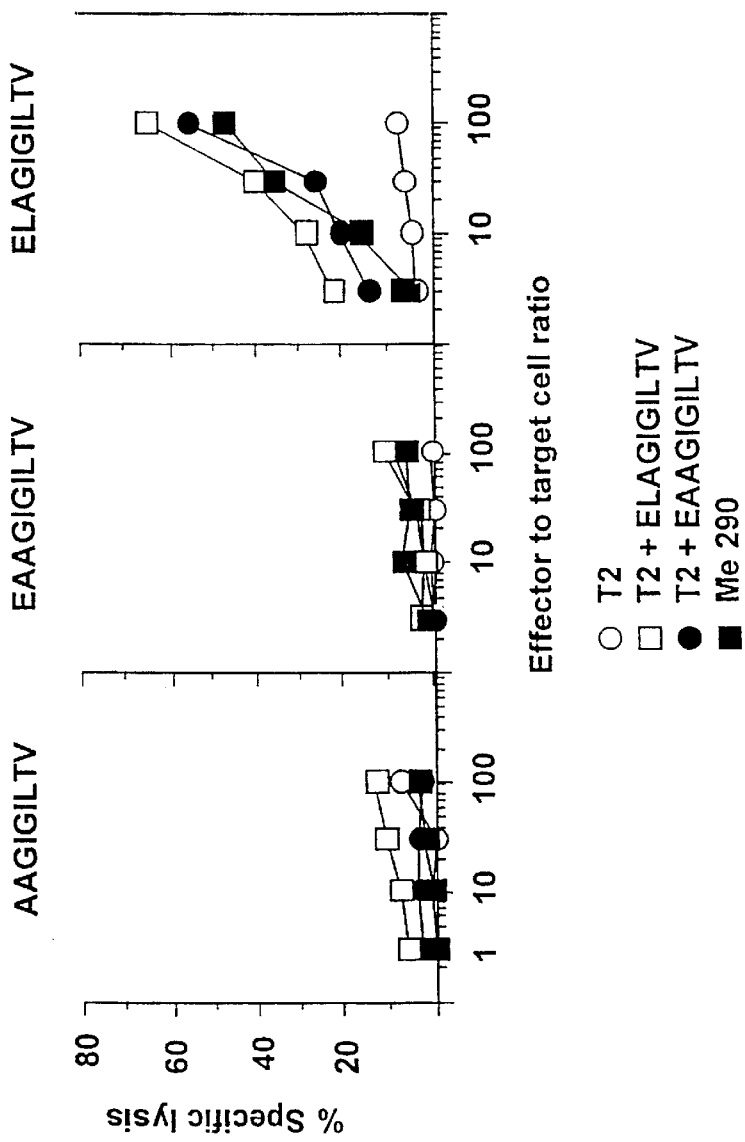
FIG. 4 parallels FIG. 3, but uses CTLs generated from PBLs by stimulation with various peptides i.e. SEQ ID NOS: 2, 1, and 9.

The results are shown in the following table and in FIG. 4. In FIG. 4, the source of CD8+ cells used was LAU203. CTL activity was assayed seven days after the second (MC-2) restimulation. Results were obtained using SEQ ID NOS: 1 and 2. These were used to permit comparison to SEQ ID NO: 9.

Note that there was barely any activity with the parental peptides in sample LAU203, while SEQ ID NO: 9 provoked a strong CTL response. This activity was also cross reactive with SEQ ID NO: 1.

The results in the following table describe experiments using the same peptides and using PBL from eight different HLA-A2 positive melanoma patents, LAU203, LAU182, LAU145, LAU86, LAU50, LAU148, LAU161 and LAU119.

TABLE IV

Recognition of peptide analogs by Melan-A specific CTL clones

| | | M77.86 | | 7.10 | | Recognition by clone M77.80 | | | | 1.13 | |
|---|---|---|---|---|---|---|---|---|---|---|---|
| SEQ ID NO: | Peptide sequence | Peptide [nM] 50% | Relative activity | Peptide [nM] 50% | Relative activity | Peptide [nM] 50% | Relative activity | Peptide [nM] 50% | Relative activity | Peptide [nM] 50% | Relative activity |
| 2 | AAGIGILTV | 15 | 1 | 50 | 1 | 300 | 1 | 300 | 1 | 4000 | 1 |
| 5 | ALGIGILTV | 90 | 0.16 | >1000 | <0.015 | >1000 | <0.03 | >1000 | <0.03 | >10000 | <0.4 |
| 6 | AMGIGILTV | >1000 | <0.015 | >1000 | <0.015 | >1000 | <0.03 | >1000 | <0.03 | >10000 | <0.4 |
| 7 | LAGIGILTV | 0.08 | 187 | 1.5 | 33 | 150 | 2 | 0.03 | 10000 | 30 | 130 |
| 8 | MAGIGILTV | 0.6 | .25 | 15 | 3 | 200 | 1.5 | 0.5 | 600 | 80 | 50 |
| 1 | EAAGIGILTV | 0.15 | 100 | 4 | 12 | 0.06 | 5000 | 600 | 0.5 | 2000 | 2 |
| 9 | EALGIGILTV | 300 | 0.05 | >1000 | <0.015 | 40 | 7.5 | >1000 | <0.3 | >10000 | <0.4 |
| 10 | EAMGIGILTV | 0.5 | 30 | 1 | 50 | 0.02 | 15000 | 5 | 60 | 50 | 80 |
| 11 | ELAGIGILTV | 0.015 | 1000 | 0.5 | 100 | 0.015 | 20000 | 0.5 | 600 | 20 | 200 |
| 12 | EMAGIGLTV | 550 | 36 | >1000 | <0.015 | 40 | 7.5 | >1000 | <0.3 | >10000 | <0.4 |
| 13 | YAAGIGILTV | 0.015 | 1000 | 35 | 1.4 | >1000 | <0.3 | 1000 | 0.3 | >10000 | <0.4 |
| 14 | FAAGIGILTV | 0.005 | 3000 | 7 | 7 | >1000 | <0.3 | >1000 | <0.3 | 200 | 20 |

Relative antigenic activity of Melan-A derived peptides was measured as described in the legend to FIG. 4 and table III.

Additional experiments are depicted in FIG. 3 which show recognition of various Melan-A peptide analogues presented by T2 cells, by TILN LAU203 and TILN LAU132. A four hour $^{51}$Cr assay was conducted at a lymphocyte to target ration of 30:1.

The first panels of FIG. 3 (top and bottom) compare SEQ ID NOS: 2, 7, 8, 5 and 6.

The second set of panels (top and bottom) compare SEQ ID NOS: 1, 9, 10, 11 and 12.

The third set (top and bottom) compares SEQ ID NOS: 1, 13, 14 and 4.

The most important result obtained herein, however, was the fact that CTLS, induced with SEQ ID NO: 9 did recognize and lyse cells presenting the endogenous peptide when SEQ ID NO: 9 was used.

Also a part of the invention are isolated cytolytic T cell lines which are specific for complexes of these peptides and their MHC binding partner, i.e., an HLA molecule, such as an HLA-A2 molecule, HLA-A*0201 being especially preferred.

The ability of these peptides to bind to HLA molecules makes them useful as agents for determining presence of HLA-A2 positive cells, such as HLA-A*0201 positive cells, by determining whether or not the peptides bind to cells in

| | | Percentage specific lysis from cultures stimulated with peptide[a] | | | | | | | | | | |
|---|---|---|---|---|---|---|---|---|---|---|---|---|
| | | SEQ ID NO: 2 Melan-A 27-35 | | | | SEQ ID NO: 1 Melan-A 26-35 | | | | SEQ ID NO:[c] Melan-A 26-35 A27L SEQ ID NO: 5 | | |
| | | tested on: | | | | | | | | | | |
| Patient code | E/T[b] | T2 | T2 + M10 | Me260 | Me290 | T2 | T2 + M10 | Me290 | Me260 | T2 | T2 + M10 | Me290 | M3260 |
| LAU 203 | 100 | 38 | 29 | 7 | 17 | 37 | 41 | 15 | 6 | 32 | 83 | 18 | 81 |
| | 30 | 29 | 11 | 10 | 0 | 17 | 23 | 7 | 1 | 26 | 96 | 4 | 75 |
| | 10 | 3 | 6 | 2 | 0 | 9 | 17 | 0 | 0 | 17 | 73 | 1 | 62 |
| LAU 132 | 100 | 9 | 12 | 1 | 0 | 19 | 19 | 6 | 3 | 34 | 50 | 6 | 31 |
| | 30 | 3 | 7 | 2 | 0 | 5 | 10 | 1 | 2 | 16 | 32 | 3 | 18 |
| | 10 | 0 | 0 | 5 | 1 | 0 | 0 | 1 | 0 | 5 | 23 | 2 | 6 |
| LAU 145 | 100 | 15 | 24 | 4 | 1 | 39 | 40 | 5 | 9 | 29 | 50 | 6 | 30 |
| | 30 | 9 | 12 | 3 | 1 | 15 | 25 | 2 | 1 | 10 | 29 | 5 | 19 |
| | 10 | 3 | 6 | 0 | 0 | 4 | 6 | 0 | 0 | 10 | 16 | 3 | 7 |
| LAU 86 | 100 | 36 | 29 | 22 | 5 | 44 | 38 | 14 | 10 | 35 | 45 | 24 | 15 |
| | 30 | 17 | 15 | 9 | 5 | 20 | 26 | 6 | 0 | 24 | 23 | 10 | 4 |
| | 10 | 16 | 5 | 2 | 0 | 10 | 10 | 1 | 0 | 14 | 9 | 1 | 0 |
| LAU 50 | 100 | 21 | 26 | 7 | 5 | 15 | 20 | 5 | 5 | 19 | 26 | 6 | 20 |
| | 30 | 7 | 16 | 4 | 5 | 8 | 13 | 1 | 0 | 10 | 18 | 3 | 8 |
| | 10 | 7 | 7 | 0 | 4 | 0 | 4 | 1 | 0 | 3 | 12 | 0 | 0 |
| LAU 148 | 100 | 51 | 39 | 13 | 4 | 46 | 45 | 9 | 0 | 34 | 39 | 9 | 4 |
| | 30 | 19 | 8 | 5 | 4 | 20 | 26 | 1 | 2 | 19 | 27 | 9 | 3 |
| | 10 | 3 | 6 | 1 | 0 | 14 | 14 | 6 | 0 | 13 | 13 | 1 | 0 |
| LAU 161 | 100 | 24 | 22 | 6 | 1 | 33 | 31 | 3 | 1 | 25 | 38 | 4 | 23 |
| | 30 | 3 | 8 | 6 | 1 | 16 | 12 | 3 | 0 | 18 | 23 | 2 | 13 |
| | 10 | 2 | 0 | 5 | 0 | 9 | 7 | 2 | 0 | 5 | 11 | 3 | 4 |
| LAU 119 | 100 | 31 | 27 | 5 | 12 | 33 | 31 | 1 | 4 | 18 | 45 | 5 | 45 |
| | 30 | 7 | 13 | 1 | 1 | 17 | 23 | 3 | 4 | 13 | 39 | 4 | 25 |
| | 10 | 4 | 0 | 0 | 0 | 9 | 12 | 1 | 0 | 7 | 17 | 2 | 16 |
| Clone 6 | 10 | 7 | 73 | 2 | 73 | | | | | | | | |
| | 3 | 3 | 74 | 0 | 61 | | | | | | | | |
| | 1 | 0 | 65 | 0 | 51 | | | | | | | | |

[a] Lytic activity was assayed 7 days after the third restimulation.
[b] Lymphocyte to target cell ratio titration was performed for every assay.
[c] Numbers represent the percent specific lysis obtained for each target. Me290 is a Melan-A and HLA-A*0201 positive melanoma cell line obtained from patient LAU203. Me260 is a HLA-A*0201 negative melanoma cell line obtained from patient LAU149 Each number represents the geometric mean of duplicate cultures. Bold face type indicate significant specific CTL. When the difference in specific lysis obtained on T2 cells in presence or in absence of Melan-A 26-35 (1 $\mu$M) or Me290 and Me260 is equal or higher than 10%. A patient is considered as responder when a significant specific lysis is detected in at least one of the cultures.
[d] Clone 6 is a Melan-A specific CTL clone derived from the TILN 289.

The foregoing examples, as will be seen, describe the various features of the invention. These include peptides which bind to HLA molecules, such as HLA-A2 molecules, exemplified by HLA-A*0201, which may also provoke proliferation of cytolytic T cells, These peptides, as will be seen from the data herein, are nonapeptides or decapeptides. As with all peptides, the first amino acid is the amino terminus, and the last one is the carboxy terminus. The peptides of the invention may be decapeptides, which have a Val moiety at the C, or carboxy terminus. They may have at the amino terminus, Tyr or Phe when the second amino acid is Ala. In another embodiment, the amino terminus is Glu followed by Ala, Leu or Met in the second and third position, and terminate with Val, wherein if position two is Ala, position three must be Met or Leu, and vice versa. The peptides having the amino acid sequences set forth in any of SEQ ID NOS:5, and 8–14 are exemplary.

a sample. This "ligand/receptor" type of reaction is well known in the art, and various methodologies are available for determining it.

A further aspect of the invention are so-called "mini genes" which carry information necessary to direct synthesis of modified decapeptides via cells into which the mini genes are transfected. Mini genes can be designed which encode one or more antigenic peptides, and are then transferred to host cell genomes via transfection with plasmids, or via cloning into vaccinia or adenoviruses. See, e.g., Zajac, et al., Int. J. Cancer 71: 496 (1997), incorporated by reference.

Also a feature of the invention is the use of these peptides to determine the presence of cytolytic T cells in a sample. It was shown, supra, that CTLs in a sample will react with peptide/MHC complexes. Hence, if one knows that CTLs are in a sample, HLA-A2 positive cells can be "lysed" by adding the peptides of the invention to HLA-A2 positive cells, such as HLA-A*0201 positive cells, and then determining, e.g., radioactive chromium release, TNF production, etc. or any other of the methods by which T cell activity is determined. Similarly, one can determine whether or not specific tumor infiltrating lymphocytes ("TILs") are present in a sample, by adding one of the claimed peptides with HLA-A2 positive cells to a sample, and determining lysis of the HLA-A2 positive cells via, e.g., $^{51}$Cr release, TNF presence and so forth.

Of course, the peptides may also be used to provoke production of CTLs. As was shown, supra, CTL precursors develop into CTLs when confronted with appropriate complexes. By causing such a "confrontation" as it were, one may generate CTLs. This is useful in an in vivo context, as well as ex vivo, for generating such CTLs.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An isolated peptide which binds to an HLA-A2 molecule and consists of ten amino acids, said isolated peptide having Val at its carboxy terminus, Glu at its amino terminus, Leu or Met at the second amino acid from the amino terminus, and Ala at the third amino acid from the N terminus (SEQ ID NO: 21).

2. The isolated peptide of claim 1, wherein the second amino acid from the N terminus is Leu.

3. The isolated peptide of claim 1, wherein the second amino acid from the amino terminus is Met.

4. An isolated peptide which binds to an HLA-A2 molecule and consists of ten amino acids, said isolated peptide having Val at its carboxy terminus, Glu at its amino terminus Ala at the second amino acid from the amino terminus and Leu of Met at the third amino acid from the N terminus (SEQ ID NO: 21).

5. The isolated peptide of claim 4, wherein the third amino acid from the N terminus is Leu.

6. The isolated peptide of claim 4, wherein the third amino acid from the N terminus is Met.

* * * * *